US012569649B2

(12) United States Patent
Tang et al.

(10) Patent No.: US 12,569,649 B2
(45) Date of Patent: Mar. 10, 2026

(54) MEDICAL APPARATUS SYSTEM

(71) Applicant: Lifetech Scientific (Shenzhen) Co., Ltd., Shenzhen (CN)

(72) Inventors: Huiqiang Tang, Shenzhen (CN); Anning Li, Shenzhen (CN); Ge Shao, Shenzhen (CN)

(73) Assignee: Lifetech Scientific (Shenzhen) Co., Ltd., Shenzhen (CN)

( * ) Notice: Subject to any disclaimer, the term of this patent is extended or adjusted under 35 U.S.C. 154(b) by 932 days.

(21) Appl. No.: 17/782,122

(22) PCT Filed: Oct. 26, 2020

(86) PCT No.: PCT/CN2020/123751
§ 371 (c)(1),
(2) Date: Jun. 2, 2022

(87) PCT Pub. No.: WO2021/120852
PCT Pub. Date: Jun. 24, 2021

(65) Prior Publication Data
US 2023/0001150 A1     Jan. 5, 2023

(30) Foreign Application Priority Data

Dec. 17, 2019    (CN) .......................... 201911300600.9

(51) Int. Cl.
*A61M 25/01*          (2006.01)
*A61B 50/20*          (2016.01)
*B65D 73/00*          (2006.01)

(52) U.S. Cl.
CPC ......... *A61M 25/0147* (2013.01); *A61B 50/20* (2016.02); *B65D 73/0021* (2013.01)

(58) Field of Classification Search
CPC ......... B65D 73/0021; A61M 25/0147; A61M 2025/015; A61B 50/20; A61B 50/30
(Continued)

(56) References Cited

U.S. PATENT DOCUMENTS 1,901,188 A * 3/1933 Phillips .............. B65D 73/0021
                                                      206/476
2,656,917 A * 10/1953 Hollis ..................... G09F 5/042
                                                      206/5
(Continued)

FOREIGN PATENT DOCUMENTS

AU        2009101225 A4 *  2/2010  ............... A01C 1/00
CN        202458712 U     10/2012
(Continued)

OTHER PUBLICATIONS

Office Action dated Oct. 28, 2022 for corresponding India Application No. 202217033826 and Translation.
(Continued)

*Primary Examiner* — Bhisma Mehta
*Assistant Examiner* — Adam J. Cermak
(74) *Attorney, Agent, or Firm* — Raymond Sun

(57)          ABSTRACT

A medical apparatus system (1000) is provided, including a medical apparatus (100) and a fixing plate (900) for fixing the medical apparatus (100). A fixing member (901, 902, 903, 1003, 1004) is formed by cutting along a trajectory (904) on the fixing plate (900); the fixing member (901, 902, 903, 1003, 1004) includes a free end (908, 9031, 10032, 10042) and a connection end (907, 9035, 10031, 10041); the connection end (907, 9035, 10031, 10041) is connected to a fixing plate body (990); the free end (908, 9031, 10032, 10042) can protrude from a plane at which the fixing plate body (990) is located. The fixing member (901, 902, 903, 1003, 1004) can surround an outer surface of the medical apparatus (100) to fix the medical apparatus (100); or the medical apparatus (100) can pass through the fixing member (901, 902, 903, 1003, 1004) and be fixed.

10 Claims, 11 Drawing Sheets

(58) Field of Classification Search
USPC .................................. 206/363–370, 461–465
See application file for complete search history.

(56) References Cited

U.S. PATENT DOCUMENTS

| | | | |
|---|---|---|---|
| 2,738,061 A * | 3/1956 | Roth | G09F 1/00 |
| | | | 206/476 |
| 2,944,665 A * | 7/1960 | Obeck | B65D 73/0021 |
| | | | 206/476 |
| 3,208,590 A * | 9/1965 | Blish | B65D 73/0014 |
| | | | 206/478 |
| 3,259,236 A * | 7/1966 | Cole | B65D 75/36 |
| | | | 47/84 |
| 3,368,564 A * | 2/1968 | Selix | A61M 25/02 |
| | | | 248/205.3 |
| 3,834,380 A * | 9/1974 | Boyd | A61M 25/02 |
| | | | 128/DIG. 26 |
| 4,023,678 A * | 5/1977 | Fiedler | A61F 6/14 |
| | | | 206/476 |
| 4,174,778 A * | 11/1979 | Klomp | B65D 73/0021 |
| | | | 206/418 |
| 4,966,590 A * | 10/1990 | Kalt | A61M 25/02 |
| | | | 128/DIG. 26 |
| 5,092,455 A * | 3/1992 | Leary | A61B 17/06133 |
| | | | 206/483 |
| 5,121,836 A * | 6/1992 | Brown | A61B 17/06138 |
| | | | 206/63.3 |
| 5,232,453 A * | 8/1993 | Plass | A61M 25/02 |
| | | | 128/DIG. 26 |
| 5,234,106 A * | 8/1993 | Transue | A61B 50/30 |
| | | | 206/483 |
| 5,266,401 A * | 11/1993 | Tollini | A61M 25/02 |
| | | | 128/877 |
| 5,351,822 A * | 10/1994 | Sinn | B65D 73/0021 |
| | | | 206/478 |
| 5,375,717 A * | 12/1994 | Roshdy | B65D 81/056 |
| | | | 206/464 |
| 5,425,445 A * | 6/1995 | Brown | A61B 17/06138 |
| | | | 206/380 |
| 5,435,438 A * | 7/1995 | Scanlon | A61B 17/06138 |
| | | | 206/227 |
| 5,438,791 A * | 8/1995 | Sherrod | A01K 97/06 |
| | | | 43/57.1 |
| 5,501,341 A * | 3/1996 | Van Es | A61M 25/002 |
| | | | 206/476 |
| 5,560,477 A * | 10/1996 | Scanlon | A61B 17/06138 |
| | | | 206/382 |
| 5,699,909 A * | 12/1997 | Foster | B65D 77/26 |
| | | | 206/370 |
| 5,797,884 A * | 8/1998 | Byrd | A61M 25/02 |
| | | | 604/174 |
| 5,915,564 A * | 6/1999 | Hsi-Chang | B65D 73/0085 |
| | | | 206/784 |
| 6,260,699 B1 * | 7/2001 | Kaplan | A61L 27/34 |
| | | | 206/339 |
| 6,447,486 B1 * | 9/2002 | Tollini | A61M 25/02 |
| | | | 604/180 |
| 7,055,694 B2 * | 6/2006 | Roshdy | A61B 50/33 |
| | | | 206/459.5 |
| 7,328,794 B2 * | 2/2008 | Lubs | A61M 25/002 |
| | | | 206/364 |
| 7,958,996 B2 * | 6/2011 | Hsu | B65D 85/04 |
| | | | 206/397 |
| 10,004,567 B2 * | 6/2018 | Dacey | B65D 77/04 |
| 10,045,830 B2 | 8/2018 | Sniffin et al. | |

| | | | |
|---|---|---|---|
| 2001/0025134 A1 * | 9/2001 | Bon | A61M 25/0144 |
| | | | 600/146 |
| 2003/0109861 A1 * | 6/2003 | Shimada | A61M 25/0147 |
| | | | 606/14 |
| 2004/0031706 A1 * | 2/2004 | Stringfield | B65D 5/6602 |
| | | | 229/131.1 |
| 2004/0059288 A1 * | 3/2004 | Webler | A61M 25/0147 |
| | | | 604/95.04 |
| 2006/0036218 A1 * | 2/2006 | Goodson | A61M 25/04 |
| | | | 604/264 |
| 2007/0129717 A1 * | 6/2007 | Brown, III | A61B 18/1492 |
| | | | 606/41 |
| 2007/0270679 A1 * | 11/2007 | Nguyen | A61M 25/0043 |
| | | | 600/585 |
| 2010/0063441 A1 * | 3/2010 | Grunewald | A61B 18/1492 |
| | | | 606/41 |
| 2010/0163435 A1 * | 7/2010 | Fischer | A61B 17/06138 |
| | | | 206/204 |
| 2011/0282176 A1 * | 11/2011 | Tegg | A61M 25/0136 |
| | | | 604/95.04 |
| 2011/0308983 A1 * | 12/2011 | Dacey | A61F 2/0095 |
| | | | 206/438 |
| 2012/0199704 A1 | 8/2012 | Taylor | |
| 2012/0277682 A1 * | 11/2012 | Corato | F16L 3/26 |
| | | | 604/179 |
| 2013/0281925 A1 * | 10/2013 | Benscoter | A61B 1/0125 |
| | | | 604/95.04 |
| 2014/0069841 A1 * | 3/2014 | Pizzato | B25H 3/026 |
| | | | 206/570 |
| 2014/0343553 A1 * | 11/2014 | Ford | A61B 17/1628 |
| | | | 606/80 |
| 2015/0307246 A1 | 10/2015 | Padwardhan | |
| 2016/0074072 A1 * | 3/2016 | McDonnell | F16B 13/06 |
| | | | 606/104 |
| 2016/0074625 A1 * | 3/2016 | Furnish | A61M 25/0133 |
| | | | 604/95.04 |
| 2016/0310225 A1 * | 10/2016 | Sniffin | A61B 50/20 |
| 2016/0317784 A1 * | 11/2016 | Zhang | A61M 25/0662 |
| 2016/0354151 A1 * | 12/2016 | Nadig | B65D 77/04 |
| 2016/0367787 A1 * | 12/2016 | Van Hoven | A61F 2/246 |
| 2017/0258614 A1 * | 9/2017 | Griffin | A61M 25/0147 |
| 2019/0216566 A1 | 7/2019 | Entabi | |

FOREIGN PATENT DOCUMENTS

| | | |
|---|---|---|
| CN | 205322506 U | 6/2016 |
| CN | 205458778 U | 8/2016 |
| CN | 205459054 U | 8/2016 |
| CN | 205459056 U | 8/2016 |
| CN | 207804380 U | 9/2018 |
| CN | 109926117 A | 6/2019 |
| CN | 208974114 U | 6/2019 |
| CN | 109965946 A | 7/2019 |
| CN | 109481027 B | 11/2020 |
| EP | 3085322 A1 | 10/2016 |
| JP | 2000 255627 A | 9/2000 |

OTHER PUBLICATIONS

Office Action dated Oct. 9, 2021 for corresponding China Application No. 201911300600.9 and Translation.
Office Action dated Mar. 9, 2022 for corresponding China Application No. 201911300600.9 and Translation.
European Search Report dated Nov. 9, 2023 for corresponding European Application No. EP 20 90 1423.
International Search Report dated Feb. 2, 2021 for corresponding PCT Application No. PCT/CN2020/123751.

* cited by examiner

A–A

MEDICAL APPARATUS SYSTEM

TECHNICAL FIELD

The present invention relates to the field of medical apparatuses, and in particular to a medical apparatus system.

BACKGROUND ART

In recent years, an interventional therapy for treating human diseases has become a new therapy. Many medical apparatuses are very expensive and easily damaged, especially during transportation, and they must be fixed and packaged to be prevented from being damaged due to shaking or vibration.

SUMMARY OF THE INVENTION

Based on this, it is necessary to provide a medical apparatus system whose stability can be ensured under the action of an external force during transportation.

One embodiment of the present invention provides a medical apparatus system, including a medical apparatus and a fixing plate for fixing the medical apparatus.

The fixing plate includes a fixing plate body and a fixing member; the fixing member is formed by cutting along a trajectory on the fixing plate; the fixing member includes a free end and a connection end; the connection end is connected to the fixing plate body; and the free end may protrude from a plane at which the fixing plate body is located.

The fixing member can surround an outer surface of the medical apparatus to fix the medical apparatus; or the medical apparatus can pass through the fixing member and be fixed.

The trajectory includes a starting end and a terminating end. When an outer contour of the fixing member overlaps the trajectory of the fixing member on the fixing plate, the starting end rotates outwardly or inwardly with respect to the fixing member to form a first arc; and the terminating end rotates outwardly or inwardly with respect to the fixing member to form a second arc.

Further, the free end of the fixing member is connected to the fixing plate body.

Further, the fixing member has a first hole, and the medical apparatus can pass through the first hole and be fixed.

Further, the fixing member further has a second hole, and the medical apparatus can pass through the first hole and the second hole in sequence and be fixed.

Further, the fixing member includes a first fixing member and a second fixing member disposed opposite to each other; the free end of the first fixing member and the free end of the second fixing member may be connected and fixed with each other.

Further, the first fixing member has a first hole, and the medical apparatus can pass through the first hole and be fixed.

Further, the second fixing member further has a second hole, and the medical apparatus can pass through the first hole and the second hole in sequence and be fixed.

Further, a cut is arranged on the fixing member, and at the cut position, the fixing member may bend along the cut.

Further, the medical apparatus includes a delivery sheath tube; the number of the fixing member is one or more; the delivery sheath tube includes a tube body and a hand shank;

a proximal end of the tube body is connected to the hand shank; and the fixing member fixes the tube body and/or the hand shank.

Further, the delivery sheath tube is an adjustable curved sheath tube which further includes a pull wire that is connected to the tube body and the hand shank.

The above-mentioned medical apparatus system includes the medical apparatus and the fixing plate for fixing the medical apparatus. The fixing member is formed by cutting along one trajectory on the fixing plate, and includes the free end and the connection end. The connection end is connected to the fixing plate body, and the free end can protrude from the plane at which the fixing plate body is located. The fixing member can surround the outer surface of the medical apparatus, or the medical apparatus can pass through the fixing member and be fixed, so that the fixing plate in the medical apparatus system has a simple structure and is easy to manufacture. In addition, the trajectory includes the starting end and the terminating end. The starting end and the terminating end respectively rotate outwardly or inwardly with respect to the fixing member to respectively form the first arc and the second arc. By designing the arcs respectively close to the starting end and the terminating end, stress can be dispersed, and concentration of the stress at a junction between the fixing member and the fixing plate is avoided, which effectively prevents tearing of the fixing member with respect to the fixing plate body caused by a high instantaneous momentum during transportation, thereby avoiding damage to the medical apparatus caused by shaking of the medical apparatus fixed on the fixing plate.

3

Figure 13:
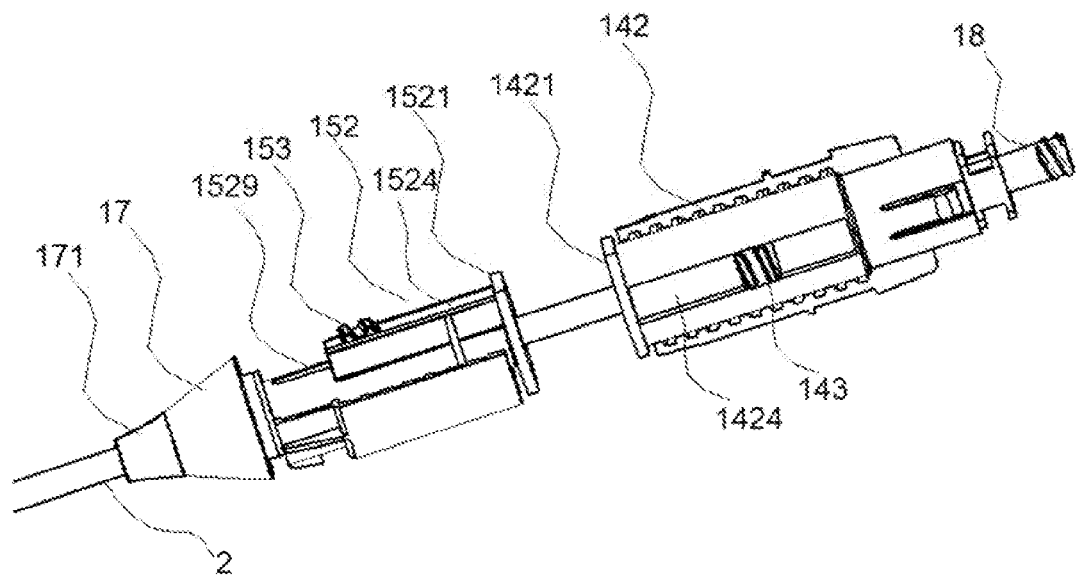

FIG. 13 is another partial schematic diagram of an adjustable curved sheath tube provided by another embodiment.

Figure 14:
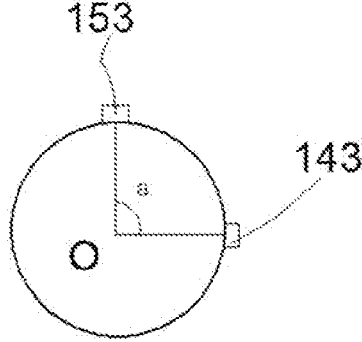

FIG. 14 is a schematic diagram of observation of FIG. 13 in a direction from a distal end to a proximal end.

Figure 15:
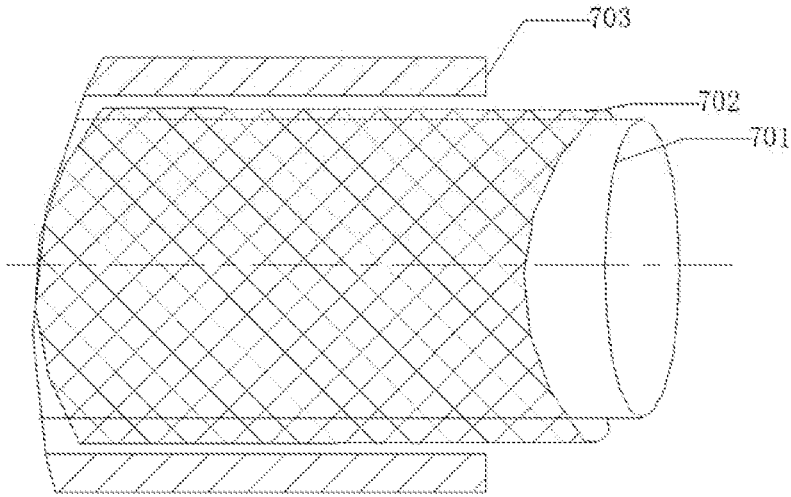

FIG. 15 is a structural enlarged diagram of part of a tube body of an adjustable curved sheath tube provided by one embodiment.

Figure 16:
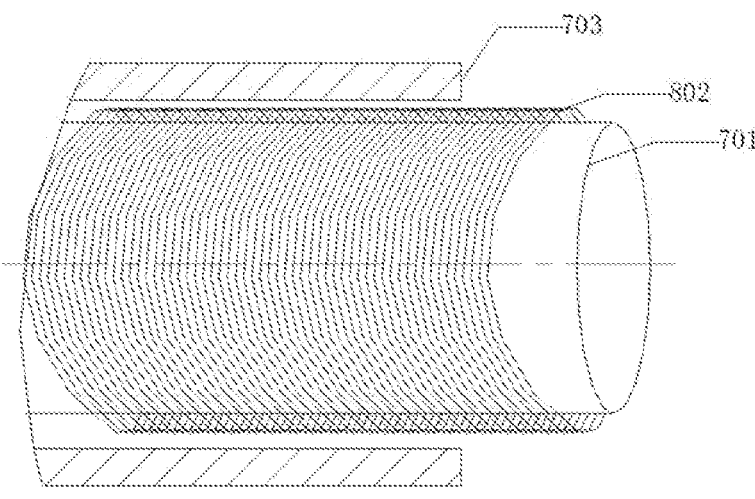

FIG. 16 is a structural enlarged diagram of part of a tube body of an adjustable curved sheath tube provided by another embodiment.

Figure 17:
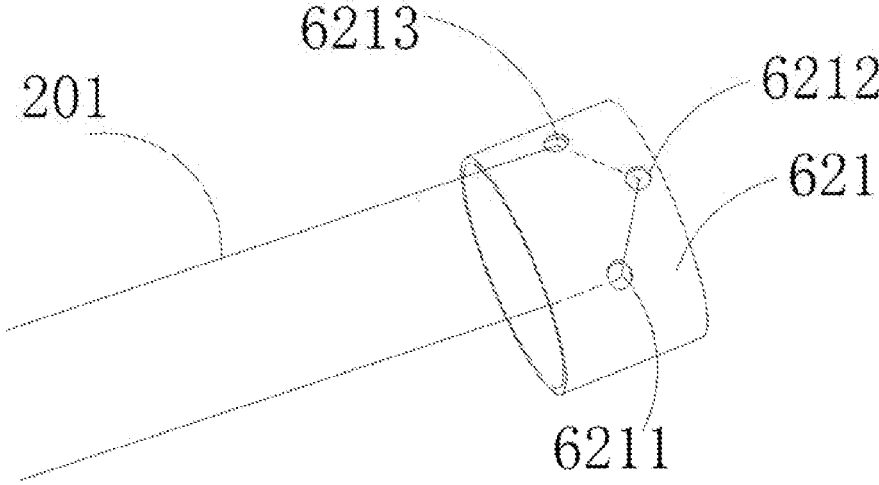

FIG. 17 is a schematic diagram showing the connection between a first pull guide wire and a first fixing ring provided by one embodiment.

Figure 18:
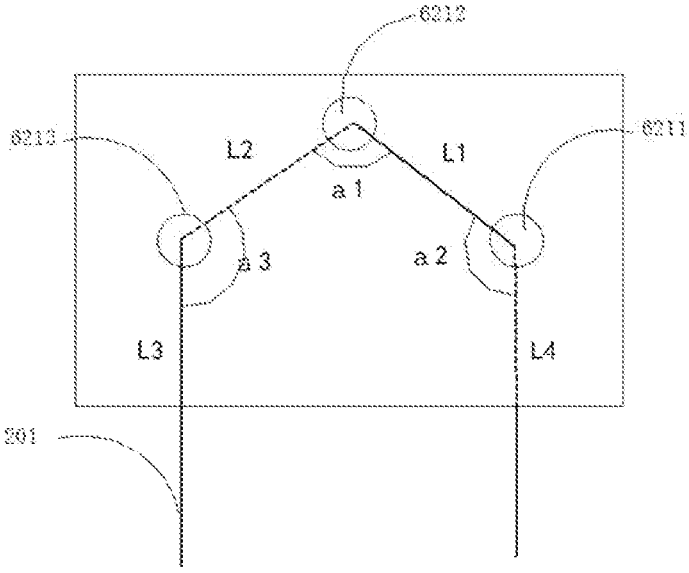

FIG. 18 is a schematic diagram of another view of FIG. 17.

Figure 19:
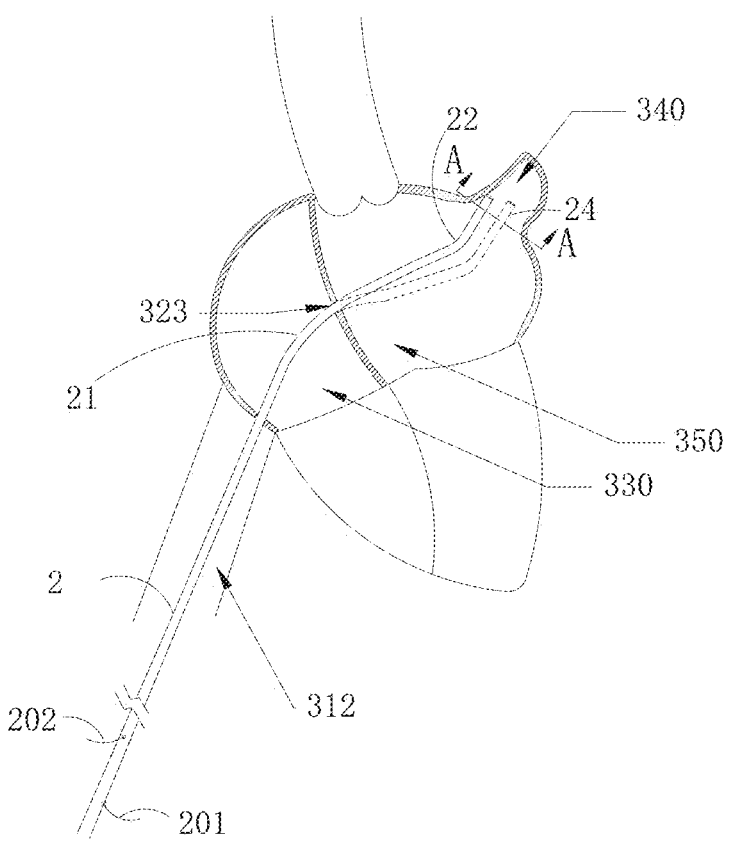

FIG. 19 is a schematic diagram showing the operation of implanting an adjustable curved sheath tube provided by one embodiment into the heart.

Figure 20:
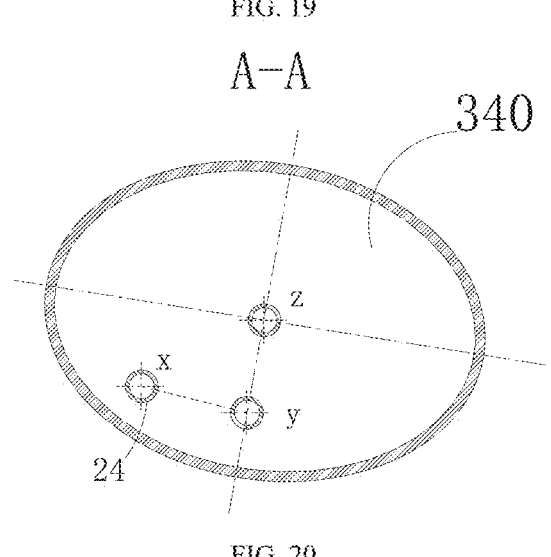

FIG. 20 is a cutaway view along line A-A in FIG. 19.

Figure 21:
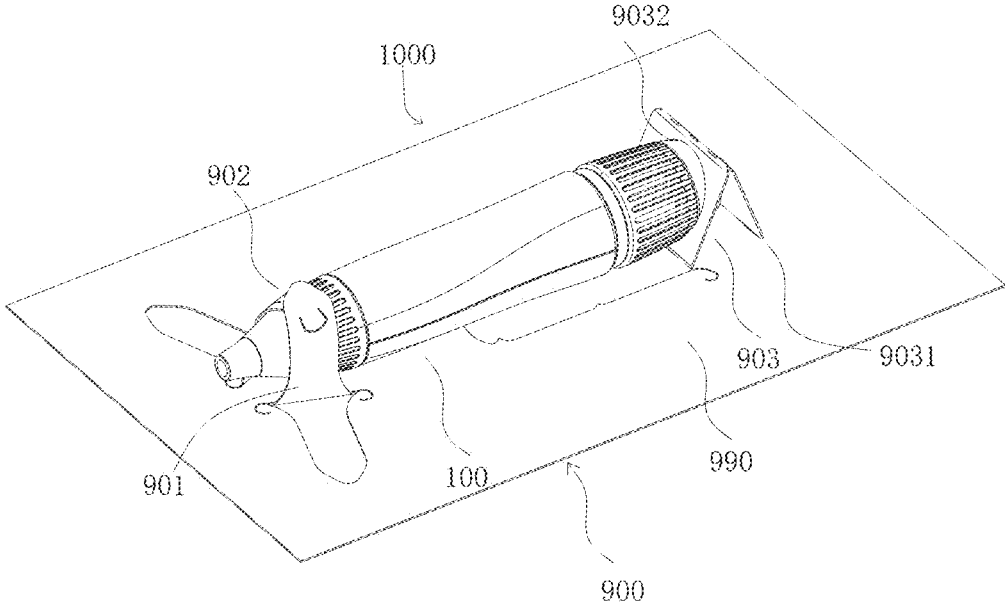

FIG. 21 is a schematic diagram of a medical apparatus system according to one embodiment.

Figure 22:
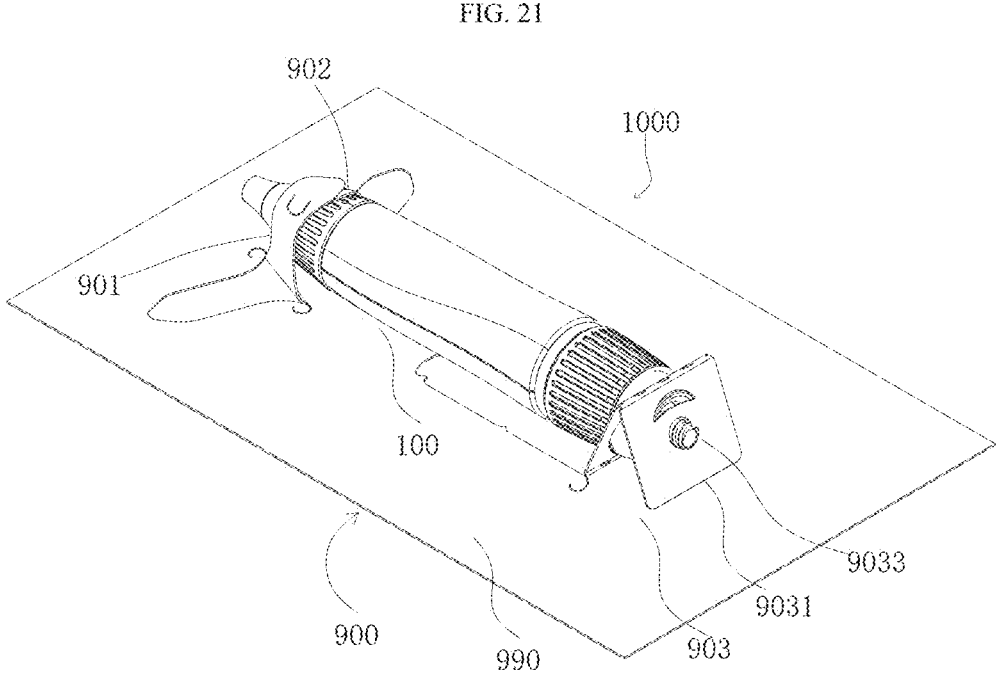

FIG. 22 is a schematic diagram of another view of FIG. 21.

Figure 23:
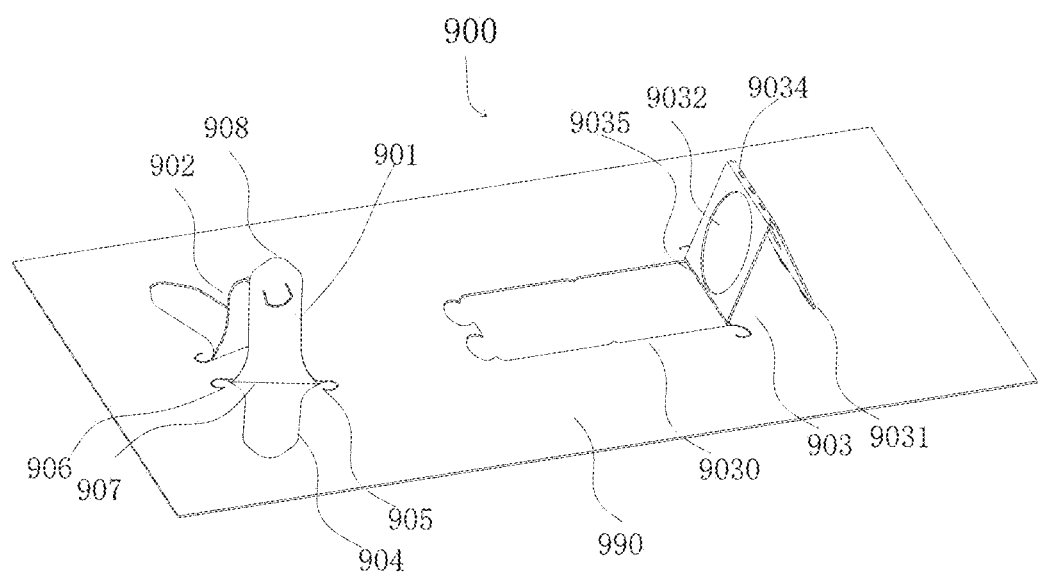

FIG. 23 is a schematic diagram of a fixing plate when a fixing member is in a used state in one embodiment.

Figure 24:
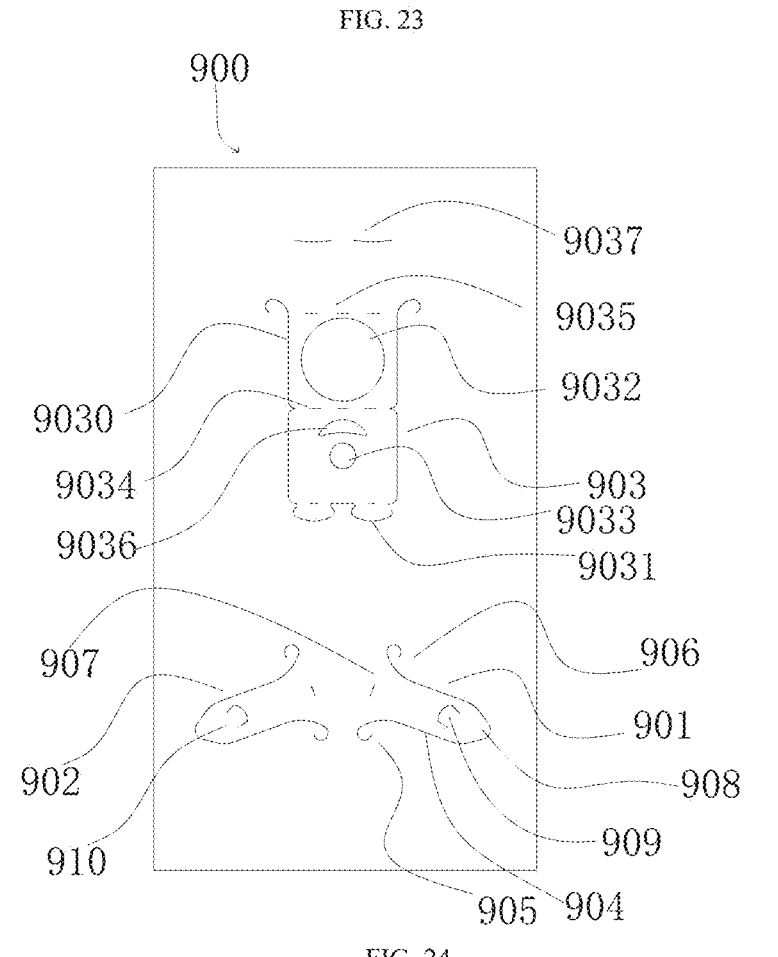

FIG. 24 is a schematic diagram of a fixing plate when a fixing member is in a manufacture-completed state (an outer contour of the fixing member overlaps a trajectory of the fixing member on the fixing plate) according to one embodiment.

Figure 25:
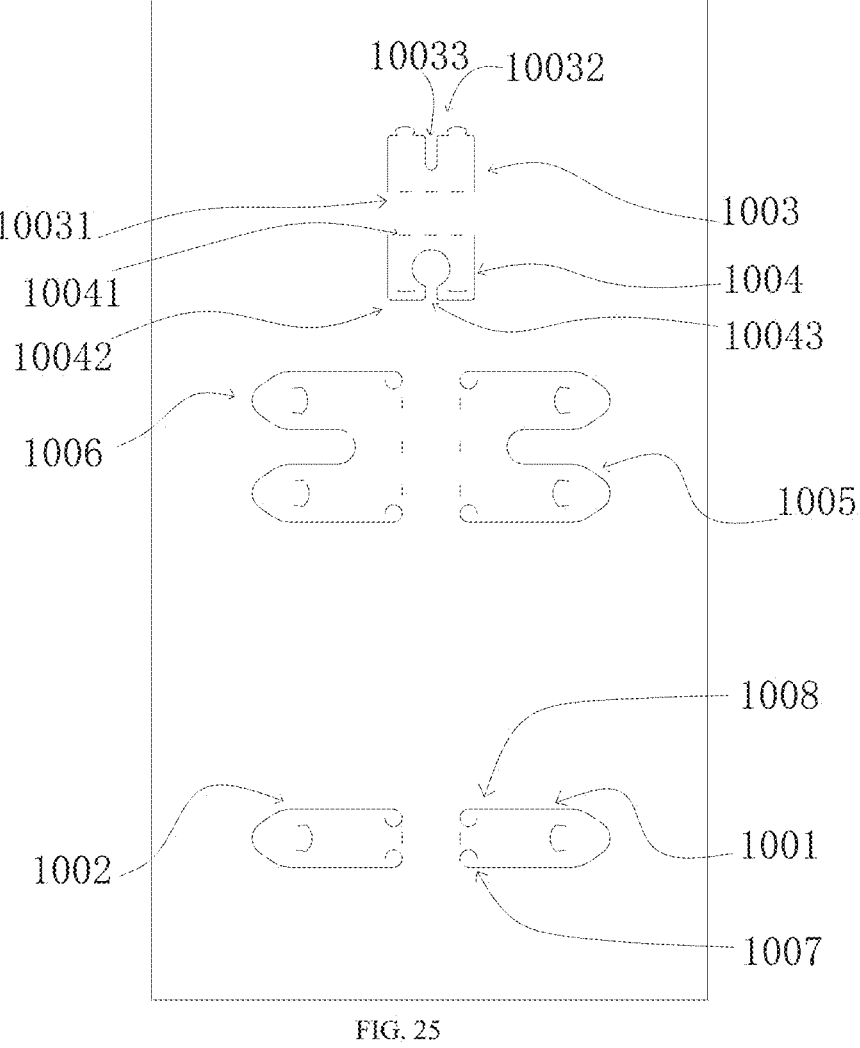

FIG. 25 is a schematic diagram of a fixing plate when a fixing member is in a manufacture-completed state (an outer contour of the fixing member overlaps a trajectory of the fixing member on the fixing plate) according to another embodiment.

DETAILED DESCRIPTION OF THE INVENTION

In order to make the foregoing objectives, features and advantages of the present invention more obvious and understandable, the specific implementation modes of the present invention are described in detail with reference to the accompanying drawings. Many specific details are described in the following descriptions to facilitate full understanding of the present invention. However, the present invention can be implemented in a variety of other ways than those described herein, and those skilled in the art can make similar improvements without departing from the connotation of the present invention. Therefore, the present invention is not limited by specific implementations disclosed below.

Unless otherwise defined, all technical and scientific terms used herein are the same as meanings of general understandings of those skilled in the art of the present invention. The terms used in the description of the disclosure herein are merely to describe the specific embodiments, not intended to limit the disclosure.

First of all, it needs to be emphasized here that a "proximal end" mentioned in the embodiments of the present invention refers to an end close to an operator during operation; a "distal end" refers to an end far away from the operator during operation; "axial" refers to a direction parallel to a connecting line between a center of a distal end and a center of a proximal end of a medical apparatus; and "radial" refers to a direction perpendicular to an axial direction.

4

Figure 1:
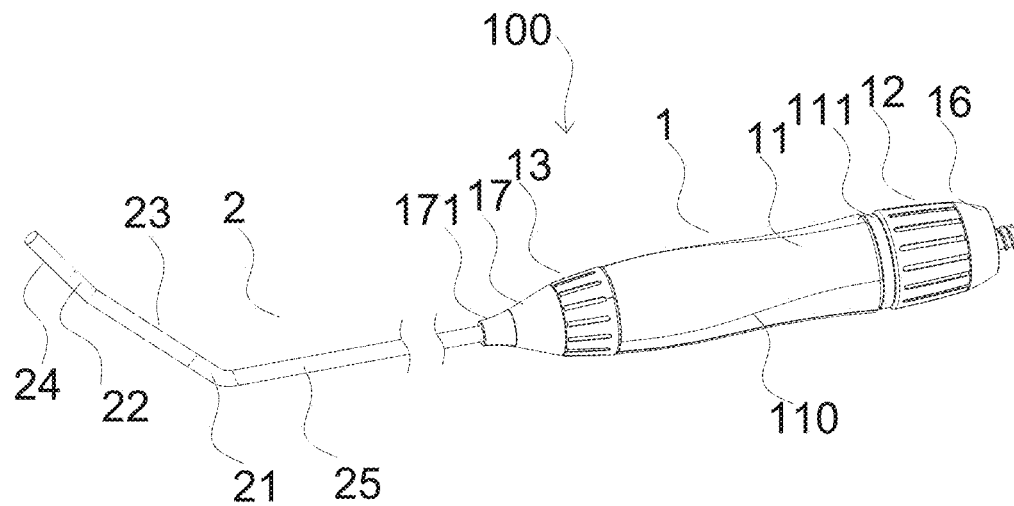
FIG. 1 is a schematic diagram of an adjustable curved sheath tube provided by one embodiment.

Referring to FIG. 1, this embodiment provides an adjustable curved sheath tube 100, including a hand shank 1 and a tube body 2. A proximal end of the tube body 2 is connected to the hand shank 1. In this embodiment, the adjustable curved sheath tube 100 is a dual-adjustable curved sheath tube, that is, the tube body 2 includes two bendable positions.

In terms of the appearance, the hand shank 1 includes a housing 11, a first curvature adjustment knob 12, a second curvature adjustment knob 13, a front end cover 17, and a rear end cover 16. The housing 11 is arranged between the first curvature adjustment knob 12 and the second curvature adjustment knob 13. A distal end of the first curvature adjustment knob 12 resists against a proximal end of the housing 11, and a proximal end of the first curvature adjustment knob 12 resists against the rear end cover 16. A proximal end of the second curvature adjustment knob 13 resists against a distal end of the housing 11, and a distal end of the second curvature adjustment knob 13 resists against the front end cover 17.

A distal end of the front end cover 17 is connected with a horn-type protective sleeve 171. The material of the protective sleeve 171 is silica gel or rubber. The proximal end of the tube body 2 extends into a proximal end of the protective sleeve 171. The protective sleeve 171 is used for avoiding breakage caused by an extremely large bending angle of part of the tube body 2 that is in contact with the protective sleeve 171.

In this embodiment, the first curvature adjustment knob 12 and the second curvature adjustment knob 13 rotate respectively with respect to the housing 11. An operator can hold the housing 11 with a hand and grasp the first curvature adjustment knob 12 or the second curvature adjustment knob 13 directly with the thumb and the index finger to rotate them, thus making the operation more convenient.

The first curvature adjustment knob 12 and/or the second curvature adjustment knob 13 will not directly resist against the housing 11. A ring 111 may be arranged between the first curvature adjustment knob 12 and/or the second curvature adjustment knob 13 and the housing 11. The ring 111 is fixedly connected to the housing 11, and the first curvature adjustment knob 12 or the second curvature adjustment knob 13 resists against the ring 111. Relative rotation between the first curvature adjustment knob 12 or the second curvature adjustment knob 13 and the ring 111 can be achieved. The fixed connection may be a fastened connection or glued fixation. Adding the ring 111 may increase the size of the hand shank 1 and also provides decoration.

In other embodiments, the first curvature adjustment knob 12 and/or the second curvature adjustment knob 13 are located in the middle part of the housing 11. That is, the middle part of the housing 11 is cut off to form a plurality of housing portions. The first curvature adjustment knob 12 and the second curvature adjustment knob 13 respectively resist against the adjacent housing parts and may rotate relative to the housing parts.

The housing ills approximately of a columnar structure. The middle part of an outer wall of the housing 11 is sunken inwardly, and an outer diameter of the middle part of the outer wall of the housing 11 is less than that of two ends of the outer wall of the housing 11, which is convenient for the operator to hold. Optionally, the outer wall of the housing 11 may be provided with an antiskid line 110 which is convenient for operation.

Figure 2:
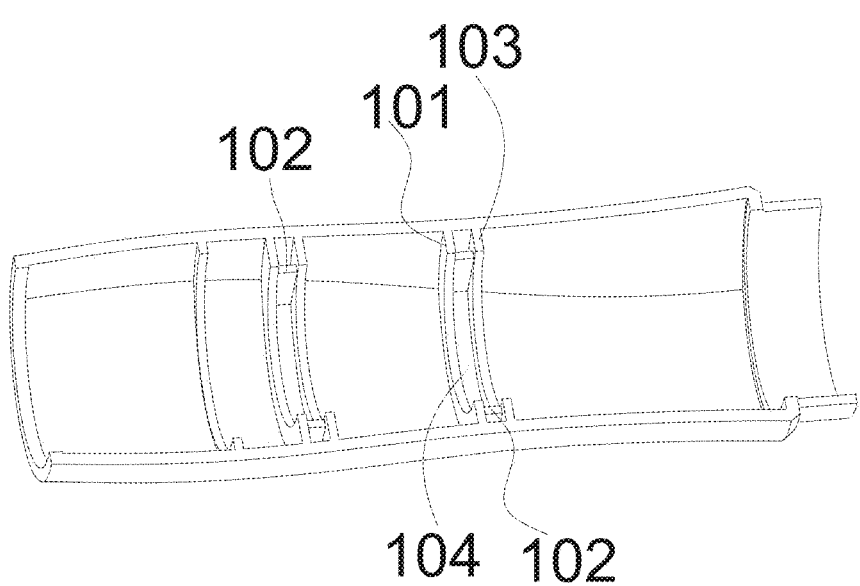
FIG. 2 is a partial schematic diagram of a housing of an adjustable curved sheath tube provided by one embodiment.

In FIG. 2, a plurality of groups of arc-shaped protrusions are arranged inside the housing 11, each group of which includes two adjacent arc-shaped protrusions 101, 103. An arc-shaped groove 104 is formed between the two adjacent arc-shaped protrusions 101, 103. Two ends of the arc-shaped groove 104 are provided with two groove stop pieces 102. In this embodiment, for facilitating machining and assembling, the housing 11 may be divided from the middle. That is, the housing includes a first housing and a second housing. A plurality of fastener structures is arranged at a junction between the first housing and the second housing. The first housing and the second housing are fastened with each other to form a columnar housing. The first housing and the second housing may also be integrated.

Figure 3:
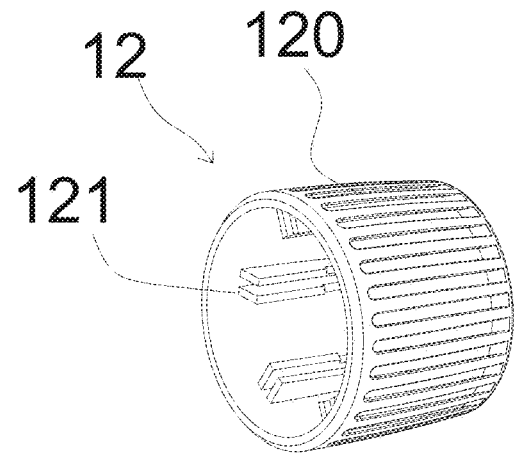
FIG. 3 is a schematic diagram of a first curvature adjustment knob of an adjustable curved sheath tube provided by one embodiment.

Referring to FIG. 3, the first curvature adjustment knob 12 is of a ring structure, and a diameter of an opening in the distal end of each ring structure and a diameter of an opening in the proximal end of the ring structure may be the same or different, which can be designed according to the appearance of the hand shank. An outer wall of the first curvature adjustment knob is provided with an antiskid member 120, such as a striped structure, a thread structure, or a convex block structure. An inner wall of the first curvature adjustment knob 12 is provided with a clamping slot structure 121. The second curvature adjustment knob 13 has the same structure as that of the first curvature adjustment knob 12. The sizes of the second curvature adjustment knob 13 and the first curvature adjustment knob 12 may be the same or different.

Figure 4:
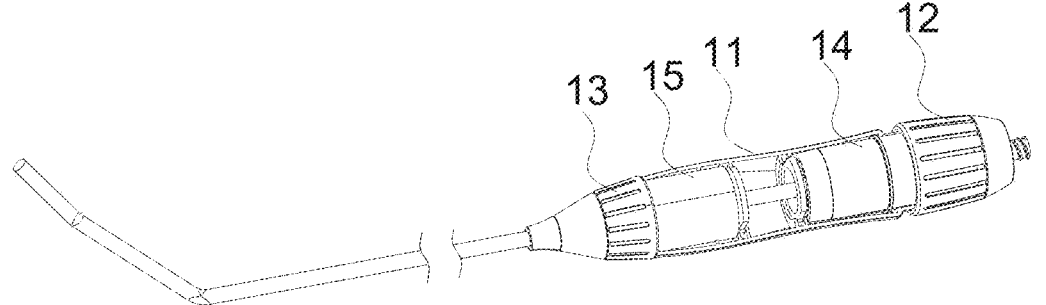
FIG. 4 is a partial schematic diagram of an adjustable curved sheath tube provided by one embodiment.

Referring to FIG. 4, the hand shank 1 further includes a first bend adjustment module 14 and a second bend adjustment module 15. A distal end of the first bend adjustment module 14 is opposite to a proximal end of the second bend adjustment module 15. The first bend adjustment module 14 is arranged in the housing 11 and the first curvature adjustment knob 12, and the second bend adjustment module 15 is arranged in the housing 11 and the second curvature adjustment knob 13.

Figure 5:
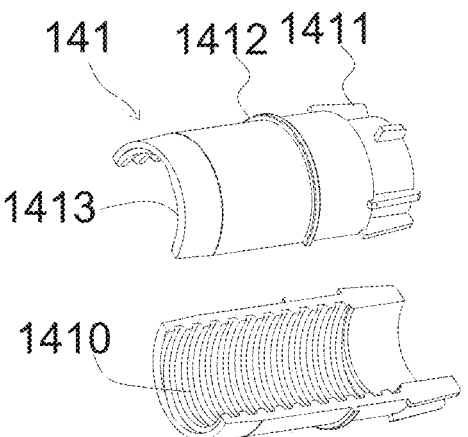
FIG. 5 is a schematic diagram of a first transmission thread bushing of an adjustable curved sheath tube provided by one embodiment.
Figure 6:
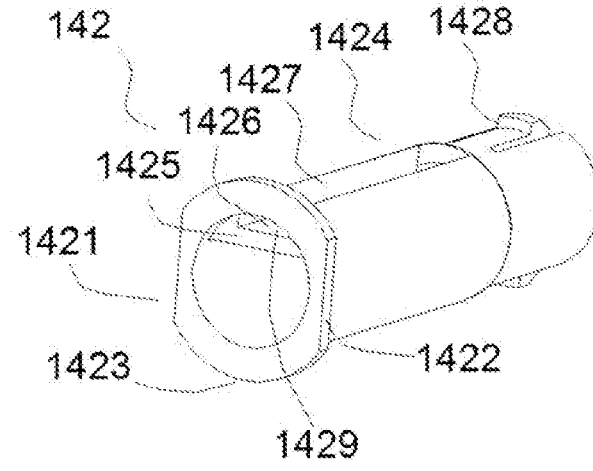
FIG. 6 is a schematic diagram of a first guide rail member of an adjustable curved sheath tube provided by one embodiment.
Figure 7:
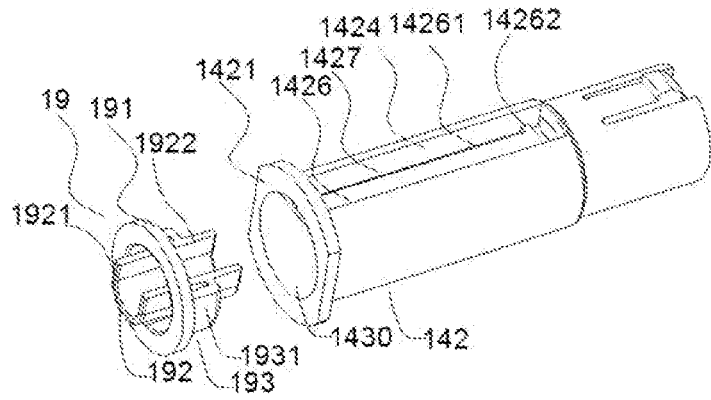
FIG. 7 is a schematic diagram of a first guide rail member and a support member of an adjustable curved sheath tube provided by one embodiment.

Referring to FIG. 5, FIG. 6, and FIG. 7, the first bend adjustment module 14 includes a first transmission thread bushing 141, a first guide rail member 142, and a first sliding block 143. The first sliding block 143 is slidably arranged on the first guide rail member 142, and the first transmission thread bushing 141 surrounds the first guide rail member 142 and the first sliding block 143.

Referring to FIG. 5, the first transmission thread bushing 141 is cylindrical. In order to facilitate machining and assembly, like the housing 11, the first transmission thread bushing 141 may be divided from the middle or may be integrated. An inner wall of the first transmission thread bushing 141 is provided with a thread structure 1410, and an outer wall of the first transmission thread bushing 141 is provided with a convex block structure 1411. With reference to FIG. 3 and FIG. 5, the convex block structure 1411 is matched with the clamping slot structure 121 on the inner wall of the first curvature adjustment knob 12 to fixedly connect the first transmission thread bushing 141 with the first curvature adjustment knob 12. It can be understood that in one embodiment, the outer wall of the proximal end of the first transmission thread bushing 141 may be provided with the clamping slot structure, and the inner wall of the first curvature adjustment knob 12 may be provided with the convex block structure. The clamping slot structure is matched with the convex block structure. In one embodiment, the first curvature adjustment knob 12 and the first transmission thread bushing 141 are directly and fixedly connected with each other by glue. In this embodiment, the convex block structure 1411 on the outer wall of the first transmission thread bushing 141 is located at the proximal end of the first transmission thread bushing 141. In other embodiments, the convex block structure 1411 may be also located at the middle part or distal end of the first transmission thread bushing 141. The position of the convex block structure 1411 is mainly set according to the position of the first curvature adjustment knob 12. In this embodiment, the outer wall of the first transmission thread bushing 141 is further provided with a ring convex block 1412. It can be understood that the inner wall of the housing 11 is provided with a groove structure matched with the ring convex block 1412, thus preventing axial movement of the first transmission thread bushing 141 in the housing 11. However, the first transmission thread bushing 141 can be allowed to rotate with respect to the housing.

In this embodiment, the first curvature adjustment knob 12 and the first transmission thread bushing 141 form a first gyration subassembly. It can be understood that in other embodiments, the hand shank 1 may not include the first curvature adjustment knob 12, and the first gyration subassembly may not include the first curvature adjustment knob 12, and only includes the first transmission thread bushing 141. The first sliding block performs a reciprocating movement on the first guide rail member by means of directly gyrating the first transmission thread bushing 141.

A distal end or proximal end of the first guide rail member is provided with a catch structure that is abutted with the housing to avoid axial and radial movements of the first guide rail member. Specifically, referring to FIG. 6, the first guide rail member 142 has a tube cavity structure. The catch structure is arranged at an opening of a distal end of the first guide rail member 142. The catch structure is a "track-type" ring protrusion portion 1421. A periphery of the "track-type" ring protrusion portion 1421 includes two sections of an arc-shaped portion 1423 and two sections of straight-line portions 1422. The arc-shaped portion 1423 and the straight-line portions 1422 are alternately connected to form an appearance similar to a "track". With reference to FIG. 2 and FIG. 6, the "track-type" ring protrusion portion 1421 is matched with the plurality of arc-shaped grooves 104 arranged inside the housing 11. Specifically, the sections of the arc-shaped portion 1423 of the "track-type" ring protrusion portion 1421 are clamped in the arc-shaped grooves 104 arranged inside the housing 11, and the straight-line portions 1422 of the "track-type" ring protrusion portion 1421 resist against the groove stop pieces 102 at the two ends of the arc-shaped grooves 104 to fix the first guide rail member 142 and the housing 11 and prevent the axial and radial movements of the first guide rail member 142. In other embodiments, the "track-type" ring protrusion portion may be replaced with a round ring protrusion portion. The two ends of the arc-shaped grooves 104 arranged inside the housing 11 may not be provided with the stop pieces, and the round ring protrusion portion is directly clamped in the arc-shaped grooves 104.

The first guide rail member 142 is arranged in the first transmission thread bushing 141. The first transmission thread bushing 141 is arranged in the housing 11. With reference to FIG. 2 and FIG. 5, a distal end 1413 of the first transmission thread bushing 141 resists against a side wall of the arc-shaped protrusion 103, close to the proximal end, of the two arc-shaped protrusions arranged inside the housing 11 to play a limiting role.

Referring to FIG. 6 again, a first groove 1424 is axially arranged on an outer wall of the first guide rail member 142; at least part of the outer wall of the first guide rail member 142 is radially sunken towards a center axis of the first guide rail member 142 to form the first groove 1424. The first groove 1424 includes a first bottom 1426 and two first side walls 1427. The first groove 1424 forms a track, a length of which determines the range of a bending angle of a bent position on the tube body. In this embodiment, the first groove 1424 is linear. In another embodiment, the first groove 1424 may also be an arc shape extending from the proximal end to the distal end. In other embodiments, the first groove 1424 may also be arranged on an outer surface of the first guide rail member 142. The first side walls 1427 are located on the outer surface of the first guide rail member 142. The first bottom 1426 is at least part of the outer surface of the first guide rail member 142.

In this embodiment, a distal end 1425 of the first groove is located at the distal end of the first guide rail member 142. The first ring protrusion portion 1421 and the distal end 1425 of the first groove 1424 are encircled to form a first opening 1429 that is used for allowing a first pull wire to pass through. The position of the distal end 1425 of the first groove that is in contact with the first pull wire may be set to be a circular-arc-shaped structure, thereby avoiding an edge of the distal end 1425 of the first groove from abrading the first pull wire, so that the service life of the first pull wire is prolonged.

In one embodiment, the distal end 1425 of the first groove may be located in the middle of the first guide rail member 142. In one embodiment, the first opening 1429 may be formed in any position on the first guide rail member 142. For example, the first opening 1429 may be formed in any position in the first groove 1424 that is close to the distal end, or the distal end of the first groove 1424, or the position of the first groove 1424 close to the proximal end, or the proximal end of the first groove 1424. Alternatively, the first guide rail member 142 may not be provided with the first opening 1429, and the proximal end of the first pull wire passes through a wall of the tube body, directly enters the first groove, and is connected to the first sliding block.

The proximal end of the first guide rail member 142 is provided with a first connection member 1428. With reference to FIG. 1 and FIG. 6, the first connection member 1428 and the first guide rail member 142 are of an integrated structure or are fixedly connected. The first connection member 1428 is screwed or fastened to the rear end cover 16.

Optionally, the first groove is provided with a slideway; the first sliding block slides on the slideway. In this embodiment, referring to FIG. 7, the slideway is a groove slideway 14261. The first bottom 1426 of the first groove 1424 is provided with two groove slideways 14261 which are parallel to the two first side walls 1427 and have approximately the same length as the first side walls 1427. In other embodiments, the groove slideway 14261 may be a curve shape or a broken line shape. The groove slideways 14261 do not need to be parallel to the two first side walls 1427. The lengths of the groove slideways 14261 and the lengths of the first side walls 1427 may also be different.

Two ends of the groove slideways 14261 are respectively provided with slideway stop pieces 14262. A surface (1436 in FIG. 10) of the first sliding block opposite to the first bottom 1426 of the first groove 1424 is provided with a protrusion sliding member (specifically referring to the structure of the first sliding block below). The first sliding block slides between the slideway stop pieces 14262 of the groove slideways 14261, so as to control a sliding range of the first sliding block and prevent the first sliding block from being separated from the first groove 1424. In this embodiment, the two groove slideways 14261 are respectively close to the two first side walls 1427. In other embodiments, at least any one of the two groove slideways 14261 may be arranged at a position of the first bottom 1426 close to the middle, or the number of the groove slideways 14261 may be one or more.

In another embodiment, the first side wall 1427 of the first groove 1424 is provided with a groove slideway, and a surface (referring to 1437 in FIG. 9 or FIG. 10) of the first sliding block opposite to the first side wall 1427 of the first groove 1424 is provided with a protrusion sliding member. The protrusion sliding member slides in the groove slideway. Two ends of the groove slideway may be respectively provided with slideway stop pieces.

In other embodiments, the slideway may also be a protrusion slideway, and the first sliding block is provided with a sliding groove cooperatively connected with the protrusion slideway. The first sliding block slides on the slideway. In other embodiments, any position on the slideway is provided with at least two slideway stop pieces. The first sliding block slides between any two slideway stop pieces.

Figure 9:
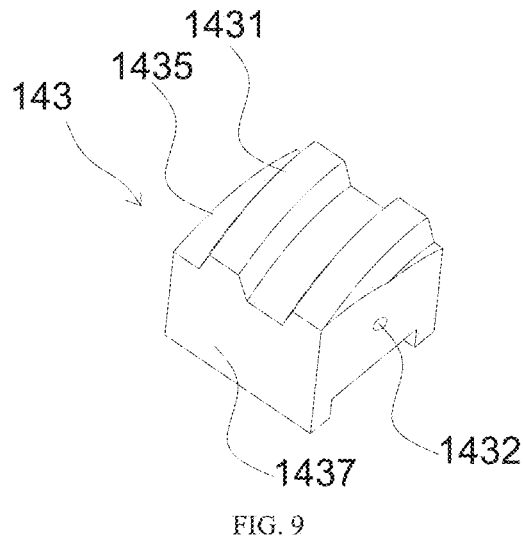
FIG. 9 is a schematic diagram of a first sliding block of an adjustable curved sheath tube provided by one embodiment.

Referring to FIG. 9, the first sliding block 143 is approximately cubic. A first surface 1435 of the first sliding block 143 is provided with a first thread structure 1431. With reference to FIG. 5 and FIG. 9, the first surface 1435 is opposite to the inner wall of the first transmission thread bushing 141. The first thread structure 1431 of the first surface 1435 of the first sliding block 143 is matched with the thread structure 1410 arranged inside the first transmission thread bushing 141.

Figure 10:
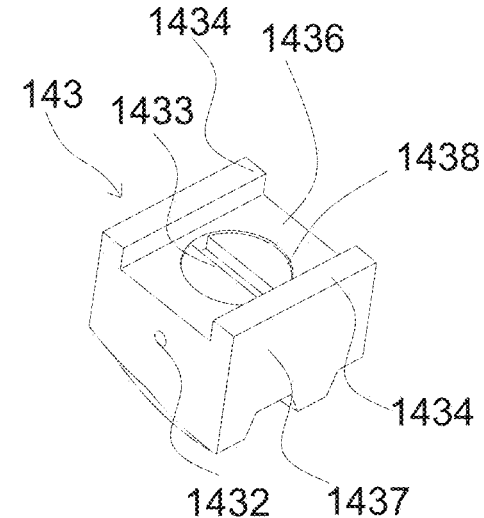
FIG. 10 is a schematic diagram of another view of a first sliding block of an adjustable curved sheath tube provided by one embodiment.

The first sliding block 143 is provided with a sliding member. With reference to FIG. 7 and FIG. 10, in this embodiment, the sliding member is a protrusion sliding member 1434. A second surface (the surface 1436 opposite to the first bottom 1426 of the first groove 1424) of the first sliding block 143 is provided with two protrusion sliding members 1434. The two protrusion sliding members 1434 are matched with the two groove slideways 14261 arranged in the first groove 1424 so that the first sliding block 143 can slide axially in the first groove 1424. By the arrangement of the sliding members 1434 and the groove slideways 14261, the contact area of the bottom of the first sliding block 143 and the first groove 1424 can be reduced, thereby reducing friction and facilitating operations.

Referring to the description of the first groove 1424 of the first guide rail member 142, in one embodiment, the sliding member includes a sliding groove. In another embodiment, the second surface of the first sliding block 143 provided with the sliding member may also be the surface 1437 opposite to the first side wall 1427 of the first groove 1424.

In FIG. 10, the first sliding block 143 is further provided with an accommodating slot 1438 and a through hole 1432. The accommodating slot 1438 communicates with the through hole 1432. A fixing member is arranged in the accommodating slot 1438. The fixing member may be a screw or a fixing member made of other materials, as long as it can be fixed in the accommodating slot 1438. In this embodiment, the fixing member is a screw 1433. One end of the first pull wire is connected with the screw 1433 after extending into the through hole 1432, thereby fixing one end of the first pull wire. In one embodiment, an opening of the accommodating slot 1438 may be formed in any surface of the first sliding block 143 except for the first surface 1435, as long as the first pull wire can be fixed. One end of the first pull wire is connected with the screw 1433 by glue. Alternatively, one end of the first pull wire is wound on the screw 1433.

Figure 11:
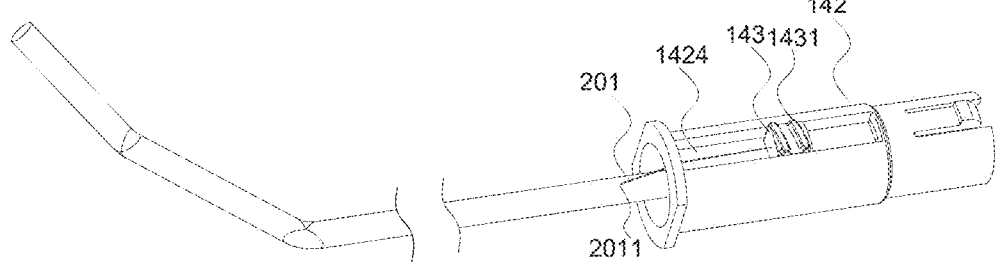
FIG. 11 is a schematic diagram showing the mutual cooperation of a first guide rail member, a first sliding block, and a tube body of an adjustable curved sheath tube provided by one embodiment.

Referring to FIG. 11, the first sliding block 143 is arranged in the first groove 1424 of the first guide rail member 142. When the first curvature adjustment knob 12 is rotated, the first transmission thread bushing 141 is driven to rotate, thus driving the first sliding block 143 to rotate. Since the first sliding block 143 is arranged in the first groove 1424 of the first guide rail member 142, the rotation of the first sliding block 143 is restrained. Therefore, the first sliding block 143 slides in a direction of the first groove 1424 of the first guide rail member 142 and will not rotate together with the first transmission thread bushing 141.

It can be understood that in one embodiment, the hand shank may not include the first curvature adjustment knob 12 and the first transmission thread bushing 141. In other ways, for example, the first sliding block 143 is directly manually operated to slide in the first groove 1424 of the first guide rail member 142, thus driving the first pull wire to move.

One end of the first pull wire 201 is fixedly connected with the first sliding block 143, and the other end of the first pull wire 201 extends towards the distal end along the first groove 1424, then passes through the distal end of the first groove 1424, and enters the tube body from an open pore 2011 in the wall of the tube body 2. The open pore 2011 is close to the distal end of the first groove 1424. As the first sliding block 143 slides, the first pull wire 201 is driven to move.

Referring to FIG. 7 again, a support member 19 is matched with the first guide rail member 142 and includes a first catch part 191, a first collecting part 192, and a second collecting part 193. The first catch part 191 and the second catch part 193 are axially connected, and the first collecting part 192 extends axially through the first catch part 191 and the second catch part 193.

The first catch part 191 has a ring structure. When the support member 19 is inserted into the first guide rail member 142, since an outer diameter of the first catch part 191 is greater than an inner diameter of the tube cavity structure of the first guide rail member 142, a proximal end face of the first catch part 191 resists against a distal end face of the "track-type" ring protrusion portion 1421 at the opening in the distal end of the first guide rail member 142. In other embodiments, the support member 19 may be arranged at a proximal portion of the first guide rail member 142, and the first catch part 191 resists against a proximal end face of the first guide rail member.

A radial section of the first collecting part 192 has approximately U-shaped structure. The first collecting part 192 is at least partially arranged in the tube cavity structure of the first guide rail member 142. In this embodiment, the first collecting part 192 includes a first portion 1921 and a second portion 1922. The first portion 1921 and the second portion 1922 are axially connected. When the support member 19 is inserted into the first guide rail member 142, due to the restriction of the first catch part 191, the first portion 1921 is arranged outside the tube cavity of the first guide rail member 142, and the second portion 1922 is arranged inside the tube cavity of the first guide rail member 142. The second portion 1922 and at least part of the first bottom 1426 of the first groove 1424 form a channel space. An axial center axis of the channel space is parallel to or coaxial with an axial center axis of the tube cavity of the first guide rail member 142. After the proximal end of the tube body passes through the channel space, the channel space can receive and support the sheath tube to further fix the proximal end of the tube body. In other embodiments, the first catch part 191 and the first collecting part 192 are axially connected, and the first collecting part 192 can also be entirely located in the tube cavity of the first guide rail member 142. In other embodiments, the first collecting part 192 may be a hollow tubular structure. The outer diameter of the tubular structure of the first collecting part 192 is the same as the inner diameter of the tube body.

Optionally, the support member 19 further includes the second catch part 193. The second catch part 193 wraps around the portion (the second portion 1922) of the first collecting part 192 arranged in the tube cavity of the first guide rail member 142. The second catch part 193 has an arc-shaped outer surface 1931. When the support member 19 is inserted into the first guide rail member 142, the second catch part 193 enters the tube cavity of the first guide rail member 142. The arc-shaped outer surface 1931 is fitted to at least part of the region of an inner surface 1430 of the tube cavity of the first guide rail member 142.

Figure 8:
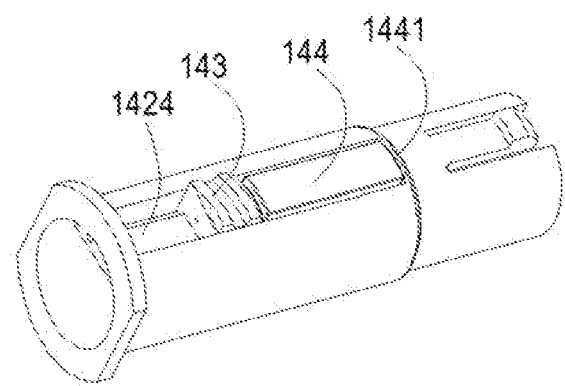
FIG. 8 is a schematic diagram of a first guide rail member, a first sliding block, and a stopper of an adjustable curved sheath tube provided by one embodiment.

When the inner diameter of the tube cavity of the first guide rail member 142 is relatively large, the diameter of the tube body is relatively small, and the outer diameter of the first collecting part 192 is relatively small, the second catch part 193 has an effect of supporting the first collecting part 192 in the tube cavity of the first guide rail member 142. In one embodiment, the first collecting part 192 and the second catch part 193 may be combined into a single component that serves as the first collecting part. When the inner diameter of the tube cavity of the first guide rail member 142, the diameter of the tube body is relatively large, and the outer diameter of the first collecting part 192 is also relatively large, the second catch part 193 may be omitted, and an outer wall of the first collecting part 192 is directly fitted to at least part of the region of the inner surface 1430 of the tube cavity of the first guide rail member 142. Optionally, the first guide rail member further includes a stopper that is arranged in the first groove to cut off the first groove, so as to restrain a sliding distance of the first sliding block, thus controlling the range of the bending angle of the tube body. For example, referring to FIG. 8, the stopper is a stop block 144. A proximal end 1441 of the stop block 144 resists against the proximal end of the first groove 1424 to adjust the length of the first groove 1424, thus controlling the sliding distance of the first sliding block 143. The number of stop blocks 144 is one. The length of the stop block 144 is adjustable. For example, the stop block may be shortened or extended. The length of the stop block 144 is adjusted to match a desired length of the first groove 1424. There can also be a plurality of stop blocks 144, when the length of each stop block 144 is different. The stop blocks 144 with different lengths are selected to match different lengths of the first groove 1424. The stopper may be a baffle plate. Two ends of the baffle plate may be clamped between the two first side walls of the first groove 1424. The sliding distance of the first sliding block is adjusted by adjusting the position of the baffle plate.

Similarly, the second bend adjustment module 15 includes a second transmission thread bushing (not shown), a second guide rail member 152, and a second sliding block 153.

Figure 12:
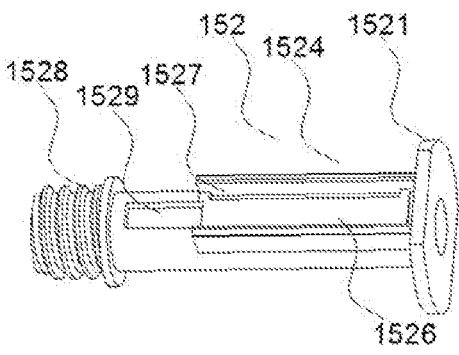
FIG. 12 is a schematic diagram of a second guide rail member of an adjustable curved sheath tube provided by one embodiment.

Referring to FIG. 12, a "track-type" ring protrusion portion 1521 is arranged at an opening of a proximal end of the second guide rail member 152. A distal end of the second guide rail member 152 is provided with a second connection member 1528. The second connection member 1528 and the second guide rail member 152 are of an integrated structure or are fixedly connected.

A second groove 1524 is axially formed in an outer wall of the second guide rail member 152. The second groove 1524 is provided on an outer surface of the second guide rail member 152. The second groove 1524 includes a second bottom 1526 and two second side walls 1527. The second side walls 1527 are located on the outer surface of the second guide rail member 152. The second bottom 1526 is at least part of the outer surface of the second guide rail member 152. In another embodiment, similar to the structure of the first groove 1424 on the first guide rail member 142, at least part of the outer wall of the second guide rail member 152 may be radially sunken towards a center axis of the second guide rail member 152.

In this embodiment, a position of the second guide rail member 152 close to the distal end of the second groove 1524 or the distal end of the second groove 1524 is provided with a second opening 1529. The second opening 1529 communicates with a tube cavity structure of the second guide rail member 152. In other embodiments, the second opening may be provided at any position on the second guide rail member 152, or no second opening is provided. The specific content refers to the first guide rail member.

In FIG. 13, one end of the second pull wire is fixedly connected with the second sliding block 153, and the other end of the second pull wire extends towards the distal end along the second groove 1524, passes through the distal end of the second groove 1524, enters the second opening 1529, extends into the outer wall of the tube body 2, and enters the tube body. As the second sliding block 153 slides, the distal end of the second pull wire is driven to move.

In this embodiment, the "track-type" ring protrusion portion 1521 arranged at the opening in the proximal end of the second guide rail member 152 is opposite to the "track-type" ring protrusion portion 1421 of the first guide rail member 142. The second connection member 1528 arranged at the distal end of the second guide rail member 152 is screwed or fastened to the front end cover 17. The proximal end of the tube body 2 extends into the protective sleeve 171 at the distal end of the front end cover 17 and then passes through the second guide rail member 152 and the first guide rail member 142 in this sequence until it is connected to a threaded connection head 18 at the proximal end. The threaded connection head 18 is used for connecting to an exhaust device.

A longitudinal direction of the second groove 1524 and a longitudinal direction of the first groove 1424 arranged on the outer wall of the first guide rail member 142 are not on the same straight line. That is, a movement trajectory of the first sliding block 143 and a movement trajectory of the second sliding block 153 are not on the same straight line. Referring to FIG. 14, in a direction from the distal end to the proximal end, in this embodiment, an included angle a between a perpendicular distance from the first sliding block 143 and an axis O of the hand shank and a perpendicular distance from the second sliding block 153 and the axis O of the hand shank is 90 degrees. In other embodiments, the included angle a is not equal to 0 degree. This arrangement aims to avoid mutual interference between the first pull wire 201 and the second pull wire (that is connected with the second sliding block 153).

In this embodiment, the second curvature adjustment knob 13 and the second transmission thread bushing form a second gyration subassembly. It can be understood that, in other embodiments, the hand shank 1 may not include the second curvature adjustment knob 13, that is, the second gyration subassembly may not include the second curvature adjustment knob 13, and only includes the second transmission thread bushing. The second sliding block performs a reciprocating movement on the second guide rail member by means of directly gyrating the second transmission thread bushing.

In this embodiment, for other structures, the second bend adjustment module 15 is the same as the first bend adjustment module 14. It can be understood that the structure in the housing 11 having a cooperative relationship with the first bend adjustment module 14 or the structure on the first curvature adjustment knob 12 is correspondingly the same structure as the structure in the housing 11 having a cooperative relationship with the second bend adjustment module 15 or the structure on the second curvature adjustment knob 13. In other embodiments, the second bend adjustment module 15 may be completely the same as the first bend adjustment module 14.

In one embodiment, the tube body of the adjustable curved sheath tube 100 may have a plurality of flexible positions, such as three or more flexible positions. The hand shank correspondingly includes three or more bend adjustment modules. The three or more bend adjustment modules are axially positioned on the same straight line, and the proximal end of the sheath tube sequentially passes through the three or more bend adjustment modules.

In one embodiment, the tube body of the adjustable curved sheath tube 100 may also have only one flexible position, and the hand shank correspondingly only includes one bend adjustment module. The proximal end of the tube body passes through the bend adjustment module.

Referring to FIG. 1 again, in this embodiment, the adjustable curved sheath tube 100 is a dual-adjustable curved sheath tube, with a distal end portion of the tube body which includes two flexible tube sections, i.e., a first tube section 21 and a second tube section 22. The first pull wire is connected to the first tube section 21, and the second pull wire is connected to the second tube section 22. The tube body 2 further includes a third tube section 23, a fourth tube section 24, and a fifth tube section 25. In FIG. 1, a connection sequence from the distal end to the proximal end is the fourth tube section 24, the second tube section 22, the third tube section 23, the first tube section 21, and the fifth tube section 25.

The hardness of the third tube section 23 is greater than that of the first tube section 21 and that of the second tube section 22. The harder third tube section 23 is arranged between the two flexible tube sections (the first tube section 21 and the second tube section 22), so that when the second pull wire drives the second tube section 22 to bend, the first tube section 21 is prevented from being driven to bend. Therefore, the second tube section 22 is prevented from affecting the curvature adjustment of the first tube section 21, thus resulting in inaccurate curvature adjustment.

The hardness of the fourth tube section 24 located at the distal end of the tube body 2 is greater than that of the second tube section 22. When the distal end of the tube body 2 is delivered to a target position (such as the left atrial appendage) by means of curvature adjustment, the fourth tube section 24 located at the distal end of the tube body 2 will not bend under the influence of the bending of the second tube section 22, so that it is easier to keep the distal end of the tube body 2 coaxial with the target position, thus achieving more accurate release.

It can be understood that when the tube body of the adjustable curved sheath tube 100 is provided with only one flexible position, the tube body includes a distal tube section, a flexible tube section, and a proximal tube section connected in sequence from the distal end to the proximal end. The pull wire is connected with the flexible tube section, and the hardness of the distal tube section is greater than that of the flexible tube section. When the flexible tube section bends, the distal tube section will not be driven to bend, so that it is easier to keep the distal end of the tube body coaxial with the target position, thus achieving more accurate release.

Referring to FIG. 15 and FIG. 16, in this embodiment, the tube body 2 is made of a composite material. The tube body 2 includes an inner-layer tube 701, an intermediate layer, and an outer-layer tube 703. The inner-layer tube 701 and the outer-layer tube 703 are tube bodies made of high-molecular materials, and the intermediate layer is a woven net tube 702 or a bourdon tube 802. The tube body 2 is of an integrated tubular structure formed by thermally melting the three layers of structures.

The inner-layer tube 701 adopts a high-molecular material with high lubricity and low friction, such as polytetrafluo-roethylene (PTFE) and high density polyethylene (HDPE), an inner surface of which is smooth, which can ensure that other apparatuses smoothly extend through the inner sur-face. The outer-layer tube 703 is formed by splicing high-molecular materials with different hardnesses, such as PEBAX with different hardnesses and polyamide (PA) tubes with different hardnesses.

The woven net tube 702 of the intermediate layer is formed by weaving a metal wire via a knitting machine. In the process of manufacturing the tube body 2, one section of woven net tube is cut down and is laced and pasted on an outer surface of the inner-layer tube 701, and the outer-layer tube 703 surrounds it for thermal melting into the integrated tube cavity structure. Similarly, the bourdon tube 802 of the intermediate layer is wound by a spring machine for winding a spring, but the process of manufacturing the tube body 2 is the same as that of the woven net tube.

In this embodiment, referring to FIG. 1 again, the tube body 2 may be pre-molded. The thermally molten tube body is placed in a plastic mold to mold a desired molding angle state. Specifically, the first tube section 21 and/or the second tube section 22 are pre-molded into curved states. Under the control of the hand shank 1, the first tube section 21 and/or the second tube section 22 is further curved within a certain radian range. In one embodiment, the tube body 2 may also be a straight tube.

A first fixing ring and a second fixing ring are arranged in the tube body 2. The first pull wire is connected to the first fixing ring; the first fixing ring is arranged at the first tube section 21; the second pull wire is connected to the second fixing ring; and the second fixing ring is arranged at the second tube section 22. The first fixing ring surrounds an outer surface of the intermediate layer of the tube body 2 and is embedded into the outer-layer tube 703 of the tube body 2.

Referring to FIG. 17, a side wall of the first fixing ring 621 is provided with a first hole 6211, a second hole 6212, and a third hole 6213. The second hole 6212 is closer to the distal end of the first fixing ring 621 than the first hole 6211 and the third hole 6213. The proximal end of the first pull wire 201 is connected to the first sliding block, and the distal end of the first pull wire 201 passes through the first hole 6211, the second hole 6212, and the third hole 6213 in sequence, or passes through the third hole 6213, the second hole 6212, and the first hole 6211 in sequence, then extends towards the proximal end along the tube body 2, and is connected to the first sliding block again.

Referring to FIG. 18, a first connecting line L1 is provided between a center of the first hole 6211 and a center of the second hole 6212, and a second connecting line L2 is provided between a center of the third hole 6213 and the center of the second hole 6212. An included angle a1 between the first connecting line L1 and the second connecting line L2 is an obtuse angle. An included angle a2 is formed between the first connecting line L1 and Section L4 of the first pull wire 201, and an included angle a3 is formed between the second connecting line L2 and Section L3 of the first pull wire 201, where a2 and a3 are both obtuse angles. In this way, stress concentration of the first pull wire can be avoided, thereby prolonging the service life.

Similarly, a side wall of the second fixing hole is provided with a fourth hole, a fifth hole, and a sixth hole. The fifth hole from among the fourth hole, the fifth hole, and the sixth hole is closer to the distal end. The structure is the same as that of the first fixing ring 621, so descriptions thereof are omitted here.

In this embodiment, a direction to which the side wall of the first fixing ring 621 provided with the first hole 6211, the second hole 6212, and the third hole 6213 faces and a direction to which the side wall of the second fixing ring provided with the fourth hole, the fifth hole, and the sixth hole faces are not the same direction. With reference to what is mentioned in the hand shank, the longitudinal direction of the second groove 1524 and the longitudinal direction of the first groove 1424 arranged on the outer wall of the first guide rail member 142 are not on the same straight line. That is, the movement trajectory of the first sliding block 143 and the movement trajectory of the second sliding block 153 are not along the same straight line. Meanwhile, the first pull wire and the second pull wire are parallel to each other in the tube body. As a whole, in addition to the above-mentioned description that the mutual interference between the first pull wire and the second pull wire can be avoided, it can be mainly implemented so that the bending directions of the first tube section 21 connected to the first pull wire and the second tube section 22 connected to the second pull wire are different, so that the tube body of the adjustable curved sheath tube 100 can bend in multiple directions and can be accurately released in a complex situation, which is conve-nient for operation.

It can be understood that the first fixing ring does not need to be provided with a hole structure. One end of the first pull wire is connected to the first sliding block, and the other end of the first pull wire passes through the first fixing ring along the inner wall of the first fixing ring, reaches the distal end of the first fixing ring, and then extends along the outer wall of the first fixing ring until it is connected to the first sliding block again. The second fixing ring may also be disposed in this way, and descriptions thereof are not provided herein.

In order to further prolong the fatigue life cycle of the connection between the pull wire and the fixing ring, a high-strength pull wire material may be used, such as a carbon fiber wire, or a high-strength NiTi multi-strand wire. Compared to a NiTi single wire with an equal outer diam-eter, the NiTi multi-strand wire has lower fatigue stress, so that when it is connected to the fixing ring, breakage caused by a concentrated fatigue stress is unlikely to occur. Even if one wire is broken, other wires may also adjust the angle of the tube body, and the service life of the pull wire can be prolonged. Meanwhile, if one wire is broken, a pre-warning sound "bang" will be made to remind an operator that "The pull wire of the adjustable curved conveying sheath tube has been broken. Be careful. End this operation process as soon as possible".

In this embodiment, a left atrial appendage occluder being released in the left atrial appendage is taken as an example. An operation process of the adjustable curved sheath tube 100 is as follows:

Referring to FIG. 19, the dual-adjustable curved sheath tube 100 reaches the right atrium 330 via the inferior vena cava 312, passes through an atrial septum puncture point 323, and reaches the left atrium 350. At this time, the fourth tube section 24 located at the distal end of the tube body 2 is fitted to the inner wall of the left atrial appendage 340. The fourth tube section 24 and the left atrial appendage 340 are not coaxial. It can be seen from FIG. 20 that the position of the fourth tube section 24 after it passes through the atrial septum 323 is x.

In order to adjust the fourth tube section 24 at the distal end of the tube body 2 to be coaxial with the left atrial appendage 340, the first curvature adjustment knob 12 on the hand shank is gyrated to apply a force to the first pull wire 201, and the first pull wire 201 adjusts the angle of the first tube section 21 so that the fourth tube section 24 moves from position x to position y to reach a lateral mid-point of the left atrial appendage 340.

The second curvature adjustment knob 13 on the hand shank is gyrated to apply a force to the second pull wire 202. The second pull wire 202 adjusts the angle of the second tube section 22 so that the fourth tube section 24 moves from position y to position z to reach the left atrial appendage 340. At this point, the fourth tube section 24 at the distal end of the tube body 2 is completely coaxial with the left atrial appendage 340, and the fourth tube section 24 at the distal end of the tube body 2 is located at position z.

When the angle and position of the tube body 2 are fixed, the operator can quickly deliver, release, and withdraw the left atrial appendage occluder. In the whole process, the operation time is short, and the safety level is high.

According to the adjustable curved sheath tube provided by this embodiment, the coaxiality of the tube body and a target lesion position is good, and the medical apparatus can smoothly reach the target lesion position. After being released, the medical apparatus can be firmly fixed in a target lesion region. Meanwhile, the dependence on the experience of the operator who delivers the medical apparatus is effectively reduced, so that the operator can use the adjustable curved sheath tube to deliver and release the medical apparatus at will after simple training.

Referring to FIG. 21 and FIG. 22, this embodiment further provides a medical apparatus system 1000. The medical apparatus system 1000 includes a medical apparatus and a fixing plate 900 for fixing the medical apparatus. In this embodiment, the medical apparatus is an adjustable curved sheath tube 100. It can be understood that in other embodiments, the medical apparatus may include various delivery sheath tubes, implantable apparatuses, or medical instruments, etc. It can be understood that the delivery sheath tube may include a tube body and a hand shank. A proximal end of the tube body is connected with the hand shank.

In this embodiment, the fixing plate 900 includes a fixing plate body 990 and a fixing member. The fixing member includes fixing members 901, 902, and 903. One end (or a central portion of the medical apparatus) of the medical apparatus is fixed by the fixing member 901 and the fixing member 902, and the other end (or the central portion of the medical apparatus) of the medical apparatus is fixed by the fixing member 903. Specifically, the fixing member 901 and the fixing member 902 respectively surround an outer surface of one end of the medical apparatus, and the other end of the medical apparatus passes through the fixing member 903. In other embodiments, one or more medical apparatuses may be fixed by one or more fixing members. When a plurality of fixing members is provided, each fixing member may have the same or different structures, which may be selected and designed according to any given need.

Referring to FIG. 23 and FIG. 24, FIG. 23 illustrates that the fixing member is in a used state, and FIG. 24 illustrates that the fixing member is in a manufacture-completed state (an outer contour of the fixing member overlaps a trajectory of the fixing member on the fixing plate).

A fixing member 901 is formed by cutting along a trajectory 904 on the fixing plate 900; the fixing member 901 includes a free end 908 and a connection end 907; the connection end 907 is connected to a fixing plate body 990; the free end 908 can protrude from a plane at which the fixing plate body 990 is located. The structure of the fixing member 902 is the same as that of the fixing member 901. The fixing member 901 has a fastener 909, and the fixing member 902 has a fastener 910. The fastener 909 and the fastener 910 may be fastened and fixed with each other. The outer surface of one end of the medical apparatus is respectively surrounded by the fixing member 901 and the fixing member 902 and is fixed. In another embodiment, only one of the fixing member 901 and the fixing member 902 is provided. After the fixing member surrounds the outer surface of the medical apparatus, the free end of the fixing member is fixed to the fixing plate body 990. The fixing method may be via fastening or gluing. In this embodiment, the trajectory 904 is in a non-closed state. The connection end of the fixing member 901 formed by cutting according to the trajectory 904 is not cut off from the fixing plate 900.

In another embodiment, in addition to the method that the medical apparatus is fixed by the two fixing members surrounding the outer surface of the medical apparatus, the medical apparatus may further pass through the two fixing members to achieve fixing. Referring to the fixing member 1003 and the fixing member 1004 in FIG. 25, the fixing member 1003 has a connection end 10031, a free end 10032, and a hole 10033, and the fixing member 1004 has a connection end 10041, a free end 10042, and a hole 10043. The free end 10032 and the free end 10042 are connected with each other (for example, via a fastener or glue), and the medical apparatus passes through the hole 10043 and the hole 10033 in sequence and is fixed. It can be understood that the hole 10043 and the hole 10033 may be an open pore or a closed hole. The shape of the hole is adapted to the shape of the medical apparatus.

Referring to FIG. 23 and FIG. 24 again, a fixing member 903 is formed by cutting according to a trajectory 9030 on the fixing plate 900; the fixing member 903 includes a free end 9031 and a connection end 9035; the free end 9031 can protrude from a plane at which the fixing plate body 990 is located; and the connection end 9035 is connected to the fixing plate body 990. The fixing member 903 has a cut 9034. After the fixing member 903 bends along the cut 9034, the free end 9031 is connected to the fixing plate body 990. The fixing plate body 990 has an opening 9037 adapted to receive the free end 9031. The free end 9031 is locked and fixed after entering the opening 9037. In other embodiments, glue may also be used. In other embodiments, the fixing member may have a plurality of cuts at different positions. The fixing member can bend along all the cuts. When the outer surface of the medical apparatus is a polyhedron shape, the bends formed by the cuts can enable the fixing member to be better fitted to the outer surface of the medical apparatus and to properly fix the medical apparatus.

The fixing member 903 has a first hole 9032 and a second hole 9033. The medical apparatus can sequentially pass through the first hole 9032 and the second hole 9033 to fix the medical apparatus. In other embodiments, the fixing member 903 can only have the first hole 9032, and the medical apparatus can pass through the first hole 9032 and be fixed. In FIG. 24, the fixing member 903 further includes a third hole 9036. The third hole 9036 is to adapt to the shape of the medical apparatus to better fix the medical apparatus on the fixing member 903.

In FIG. 24, the trajectory 904 includes a starting end 905 and a terminating end 906. The starting end 905 rotates outwardly with respect to the fixing member 901 (at this time, an outer contour of the fixing member overlaps the trajectory of the fixing member on the fixing plate) to form a first arc, and the terminating end 906 rotates outwardly with respect to the fixing member 901 (at this time, the outer contour of the fixing member overlaps the trajectory of the fixing member on the fixing plate) to form a second arc. In other embodiments, referring to FIG. 25, the starting ends of the fixing members 1001, 1002, 1005, and 1006 rotate inwardly (at this time, the outer contour of the fixing member overlaps the trajectory of the fixing member on the fixing plate), specifically referring to the fixing member 1001. The starting end 1007 and the terminating end 1008 forming the trajectory of the fixing member 1001 rotate inwardly with respect to the fixing member 1001 (at this time, the outer contour of the fixing member overlaps the trajectory of the fixing member on the fixing plate). In other embodiments, any one of the starting ends and the terminating ends forming the trajectory of the fixing member rotates inwardly (at this time, the outer contour of the fixing member overlaps the trajectory of the fixing member on the fixing plate) with respect to the fixing member, and the other one rotates outwardly (at this time, the outer contour of the fixing member overlaps the trajectory of the fixing member on the fixing plate) with respect to the fixing member.

By designing the arcs to be respectively close to the starting end and the terminating end, stress can be dispersed, and concentration of the stress at a junction between the fixing member and the fixing plate is avoided, which effectively prevents tearing of the fixing member with respect to the fixing plate caused by a high instantaneous momentum during the transportation, thereby avoiding damage to the medical apparatus caused by shaking of the medical apparatus fixed on the fixing plate.

It can be understood that when one medical apparatus is fixed, in the same fixing plate 900, the starting end and the terminating end of one part of the fixing member can be provided with the arcs, and the starting end and the terminating end of one part of the fixing member are provided with no arcs.

The technical features of the embodiments described above can be arbitrarily combined. In order to make the description concise, all possible combinations of various technical features in the above embodiments are not completely described. However, the combinations of these technical features should be considered as the scope described in this specification as long as there is no contradiction in them. The above-mentioned embodiments only express several implementation modes of the present invention, and their descriptions are more specific and detailed, but they cannot be understood as limiting the patent scope of the present invention. It should be noted that those of ordinary skill in the art can further make various transformations and improvements without departing from the concept of the disclosure, and these transformations and improvements all fall within the protection scope of the present invention. Therefore, the protection scope of the patent of the present invention shall be subject to the appended claims.

The invention claimed is:

1. A medical apparatus system, comprising a medical apparatus having an outer surface, a distal end, and a proximal end, and a fixing plate for fixing the medical apparatus, wherein:

the fixing plate comprises a proximal fixing member, a fixing plate body, and a distal fixing member;

the distal fixing member includes a first fixing member and a second fixing member, each of the first fixing member and the second fixing member comprises a free end and a connection end;

the connection ends of the first fixing member and the second fixing member are connected to the fixing plate body;

the free ends of the first fixing member and the second fixing member protrude from a plane at which the fixing plate body is located, and each of the first fixing member and the second fixing member is formed by cutting along a trajectory on the fixing plate;

the first fixing member and the second fixing member are respectively located on both sides of the medical apparatus and together surround the outer surface of the medical apparatus, and the free ends of the first fixing member and the second fixing member are connected and fixed to each other to fix a portion of the medical apparatus near the distal end of the medical apparatus in a radial direction; and the proximal fixing member includes a third fixing member which has a surface that includes a hole to enable the medical apparatus to pass through the hole and fix a portion of the medical apparatus near the proximal end of the medical apparatus in an axial direction through the hole.

2. The medical apparatus system according to claim 1, wherein the trajectory comprises a starting end and a terminating end; when an outer contour of the first fixing member overlaps the trajectory of the first fixing member on the fixing plate, the starting end rotates outwardly or inwardly with respect to the first fixing member to form a first arc; and the terminating end rotates outwardly or inwardly with respect to the first fixing member to form a second arc.

3. The medical apparatus system according to claim 1, wherein the trajectory comprises a starting end and a terminating end; when an outer contour of the second fixing member overlaps the trajectory of the second fixing member on the fixing plate, the starting end rotates outwardly or inwardly with respect to the second fixing member to form a first arc; and the terminating end rotates outwardly or inwardly with respect to the second fixing member to form a second arc.

4. The medical apparatus system according to claim 1, wherein the hole is a second hole, and the first fixing member and the second fixing member together define a first hole, and the medical apparatus passes through the first hole and the second hole in sequence.

5. The medical apparatus system according to claim 4, wherein there are two second holes, and the proximal end of the medical apparatus passes through the two second holes in sequence and is fixed.

6. The medical apparatus system according to claim 5, wherein the proximal fixing member also includes a third hole to accommodate the shape of the medical apparatus such that the medical apparatus is attached and fixed to the proximal fixing member.

7. The medical apparatus system according to claim 5, wherein a cut is arranged on the proximal fixing member, and at the cut position, the proximal fixing member bends along the cut; and the two second holes are located on either side of the cut of the proximal fixing member.

8. The medical apparatus system according to claim 1, wherein the first fixing member has a first fastener, and the second fixing member has a second fastener; the first fastener and the second fastener may be fastened and fixed with each other.

9. The medical apparatus system according to claim 1, wherein the medical apparatus comprises a delivery sheath tube; the delivery sheath tube comprises a tube body and a hand shank; a proximal end of the tube body is connected to the hand shank; and, the proximal fixing member fixes the proximal end of the hand shank and the distal fixing member fixes the distal end of the hand shank.

10. The medical apparatus system according to claim 9, wherein the delivery sheath tube is an adjustable curved sheath tube which further comprises a pull wire that is connected to the tube body and the hand shank.

* * * * *